United States Patent [19]

Krogh

[11] Patent Number: 4,601,860
[45] Date of Patent: Jul. 22, 1986

[54] METHOD FOR PRODUCING SELENOETHERS FROM SELENOALCOHOLS OR THEIR SALTS, AND CARBONATES

[75] Inventor: James A. Krogh, Mount Prospect, Ill.

[73] Assignee: PPG Industries, Inc., Pittsburgh, Pa.

[21] Appl. No.: 422,243

[22] Filed: Sep. 23, 1982

[51] Int. Cl.$^4$ ........................................... C07C 163/00
[52] U.S. Cl. ..................................................... 260/550
[58] Field of Search ......................................... 260/550

[56] References Cited

U.S. PATENT DOCUMENTS

| | | | |
|---|---|---|---|
| 2,448,767 | 9/1948 | Carlson | 260/284 |
| 2,987,555 | 6/1961 | Davis | 260/613 |
| 3,489,774 | 1/1970 | Kuhn et al. | 260/550 |
| 4,192,949 | 3/1980 | Merger et al. | 560/67 |
| 4,310,708 | 1/1982 | Strege et al. | 568/45 |
| 4,341,905 | 7/1982 | Strege | 568/45 |

OTHER PUBLICATIONS

Theilheimer, Synthetic Methods, 32/1978, p. 245, No. 536.
Y. Tamura et al., Abstract of Synthesis 1975, 641, Thioethers from Mercaptans and Carbonic Acid Esters.
Reich and Shah, "Organoselenium Chemistry . . . ", *Journal of the American Chemical Society*, vol. 97, No. 11 (May 28, 1975), pp. 3250-3252.
Clive, "Modern Organoselenium Chemistry", Tetrahedron Report No. 50, Tetrahedron, vol. 34, pp. 1049-1132 (1978).
Tamura et al, "An Alternative Method for the Preparation of Unsymmetrical Sulfides", *Synthesis*, (1975), pp. 641-642.

*Primary Examiner*—Donald G. Daus
*Assistant Examiner*—William A. Teoli, Jr.
*Attorney, Agent, or Firm*—George D. Morris

[57] ABSTRACT

Organic selenoether is produced by reacting organic selenol or salt thereof with organic carbonate.

19 Claims, No Drawings

METHOD FOR PRODUCING SELENOETHERS FROM SELENOALCOHOLS OR THEIR SALTS, AND CARBONATES

Organic selenoethers, also known as organic selenides, are useful intermediates in the preparation of olefinically unsaturated compounds, including olefinic hydrocarbons, diolefinic hydrocarbons, allylic alcohols, alpha,beta-unsaturated nitriles, olefinic ketones, exomethylene lactones and styrenes. See H. J. Reich and S. K. Shaw, "Organoselenium Chemistry . . . ", *Journal of the American Chemical Society*, volume 97, number 11, (1975) pages 3250-3252 and the references cited therein, all of which, in their entireties, are incorporated herein by reference. These olefinically unsaturated compounds, especially the olefinic hydrocarbons, the diolefinic hydrocarbons, the allylic alcohols and the styrenes, are useful as monomers in the formation of polymers by addition polymerization techniques known to the art. See also D. L. J. Clive, "Modern Organoselenium Chemistry", *Tetrahedron*, volume 34, Pergamon Press (1978), pages 1049-1132, which in its entirety is incorporated herein by reference.

It is frequently desired to convert organic selenol, also known as selenoalcohol, or a salt thereof, to organic selenoether. It has now been discovered that many organic carbonates are useful to effectuate this conversion. Accordingly, the present invention is a method comprising reacting organic selenol or a salt thereof with organic carbonate to produce organic selenoether.

The organic carbonate used in the process is subject to wide variation and may be represented by the formula $$R_1OCOR_2 \quad \text{(I)}$$
$$\parallel$$
$$O$$

wherein $R_1$ and $R_2$ are each independently monovalent organic groups which may be the same or different. The alpha carbon of at least one of $R_1$ and $R_2$ should be substantially sterically unhindered so that one of these groups may replace the selenol hydrogen or the selenol metal to form the selenoether.

Typically $R_1$ is alkyl, alpha,beta-saturated alkenyl, aralkyl, (cycloalkyl)alkyl, cycloalkyl or lower aryl, and $R_2$ is alkyl, alpha,beta-saturated alkenyl, aralkyl or (cycloalkyl)alkyl.

When alkyl is employed, it usually has from 1 to about 20 carbon atoms, often from 1 to about 10 carbon atoms. Lower alkyl having from 1 to about 4 carbon atoms is preferred. Methyl and ethyl are especially preferred. The alpha,beta-saturated alkenyl used generally has from 3 to about 10 carbon atoms; allyl is preferred. When aralkyl is employed, the aryl portion generally contains from 6 to about 10 carbon atoms and the alkyl portion usually contains from 1 to about 10 carbon atoms; benzyl is preferred. When (cycloalkyl)alkyl is used, the cycloalkyl portion generally contains from about 6 to about 8 carbon atoms and the alkyl portion typically contains from 1 to about 10 carbon atoms; cyclohexylmethyl is preferred. The cycloalkyl typically has from about 6 to about 8 carbon atoms; cyclohexyl is preferred. The lower aryl usually has from 6 to about 10 carbon atoms; phenyl is preferred. These groups are usually unsubstituted, although one or more minor substituents which do not render the organic carbonate unsuitable for its intended purpose may be present on any of the groups. Similarly, those groups having one or more rings are usually homocyclic, but one or more hetero atoms may be present so long as they do not seriously interfere with selenoether formation. The aliphatic groups and the aliphatic portions of hybrid groups such as aralkyl may be straight or branched, but it is preferred they be straight. Only one organic carbonate or a plurality of organic carbonates may be used as desired.

When a mixed organic carbonate, that is, an organic carbonate wherein $R_1$ and $R_2$ differ, is employed, it has been found that the reaction generally favors replacement of the selenol hydrogen or the selenol metal by the organo group having the less sterically hindered alpha carbon. It is ordinarily no impediment if the alpha carbon of one of $R_1$ and $R_2$ is substantially sterically hindered, but the degree of steric hinderance of the alpha carbon of at least one of $R_1$ and $R_2$ should not be so great as to preclude selenoether formation, that is to say, the alpha carbon of at least one of $R_1$ and $R_2$ should be substantially unhindered.

Examples of organic carbonates which may be employed include dimethyl carbonate, ethyl methyl carbonate, diethyl carbonate, propyl methyl carbonate, isopropyl methyl carbonate, isopropyl ethyl carbonate, butyl methyl carbonate, secondary-butyl methyl carbonate, isobutyl methyl carbonate, tertiary-butyl methyl carbonate, cyclohexyl methyl carbonate, benzyl methyl carbonate, phenyl methyl carbonate and diallyl carbonate. It is preferred that at least one of $R_1$ and $R_2$ be methyl or ethyl. The particularly preferred organic carbonates are dimethyl carbonate, diethyl carbonate and diallyl carbonate.

The organic selenol or its salt used in the process may be widely varied, and may be represented by the formula $$R_3SeM \quad \text{(II)}$$

wherein $R_3$ is a monovalent organo group and M is hydrogen, a monovalent metal or a monovalent fractional part of a polyvalent metal. Substantially any organo group which does not preclude selenoether formation may be used for $R_3$. It may be simple or it may be highly complex. Examples of organo groups which may be used include alkyl, alkenyl, aryl, (cycloalkyl)alkyl aralkyl and cycloalkyl. Such groups may be substituted or unsubstituted. They may themselves be inert to the conditions of the reaction or they may contain groups, such as mercapto, hydroxyl, amino or selenyl, which may be reactive with organic carbonate. When an aryl group or a group containing an aryl portion is used, it may be homocyclic or heterocyclic; it may comprise a single ring or it may comprise a ring assembly. Only one organic selenol or salt thereof may be employed, or a plurality of such materials may be used, as desired.

The identity of M may vary widely. Typically M is hydrogen, alkali metal or the monovalent fractional part of alkaline earth metal. Hydrogen, sodium or potassium are most frequently used.

The reaction of organic selenol or salt thereof with organic carbonate is usually conducted in the liquid phase. It may be carried out batchwise, continuously, semibatchwise or semicontinuously. When the organic carbonate is a liquid under the conditions of the reaction, it often acts as a solvent for the organic selenol or salt thereof. Typically, but not necessarily, excess organic carbonate is employed and this usually serves to solvate the organic selenol or salt thereof throughout the reaction. In many cases, one or more by-products of the reaction, most notably alcohols, also tend to solvate the organic selenol or salt thereof. Although extrinsic solvent is not ordinarily employed, it may be used when desired or when necessary to dissolve one or more of the reactants. Examples of suitable extrinsic solvents include methanol, ethanol, acetonitrile, benzene, toluene, dioxane, dimethylformamide and chlorinated solvents such as chloroform, methylene chloride, ethylene chloride, carbon tetrachloride and chlorobenzene. Only one extrinsic solvent or a plurality of extrinsic solvents may be used as desired. For many reactions, extrinsic solvent need not be introduced, and the reaction may be neat.

When extrinsic solvent is used, the weight ratio of extrinsic solvent to the selenol or salt thereof initially present is subject to wide variation. Generally, the amount of solvent should be sufficient to solvate the reactants at the reaction temperature. The weight ratio of extrinsic solvent, when used, to the organic selenol or salt thereof initially present is usually in the range of from about 0.01:1 to about 20:1. From about 0.1:1 to about 5:1 is preferred.

The temperatures at which the reaction is conducted may vary considerably, but ordinarily they are in the range of from about 0° C. to about 100° C. Temperatures in the range of from about 20° C. to about 60° C. are preferred.

The pressures at which the reaction is conducted are similarly susceptible to wide variation. Atmospheric and superatmospheric pressures are generally employed, although subatmospheric pressures may sometimes be used. Generally the pressure is in the range of from about zero to about 2500 kilopascals, gauge, but higher pressures may be used. Preferably the pressure is in the range of from about zero to about 1000 kilopascals, gauge.

The reaction may be conducted in the presence of catalyst although in many instances the use of catalyst is not needed. Exemplary catalysts which may be used include nitrogen-containing heterocyclic catalysts such as pyridine, 4-(dimethylamino)pyridine, imidazole, 2,6-lutidine and 2,4,6-collidine. Only a single catalyst or a mixture of catalysts may be used where desired. The preferred catalyst is 4-(dimethylamino)pyridine.

The equivalent ratio of the catalyst, when used, to the organic selenol or its salt initially present may vary widely, but usually it is in the range of from about 0.005:1 to about 0.5:1. It is preferred that the equivalent ratio be in the range of from about 0.01:1 to about 0.2:1.

Following preparation, the organic selenoether may be recovered from the reaction mixture by any of the various techniques known to the art. Distillation at reduced pressure is one such technique that is frequently employed.

The present invention is especially useful for the alkylation of organic selenols or salts of organic selenols to produce the corresponding alkyl selenoethers. In such cases at least one of $R_1$ and $R_2$ in Formula I, above, is alkyl. Dialkyl carbonates are preferred for these alkylations.

The invention is further described in conjunction with the following example which is to be considered illustrative rather than limiting.

EXAMPLE

A flask equipped with an agitator, a reflux condenser and an electric heating mantle was charged with 100 cubic centimeters of tetrahydrofuran and 6.24 grams of diphenyl diselenide. After the diphenyl diselenide had dissolved, 0.93 gram of sodium metal was added. The reaction mixture has heated to reflux with stirring and maintained at reflux for 5 hours. A copious amount of off-white precipitate was formed. The reaction mixture was cooled to ambient temperature and filtered. The separated precipitate was then dried for 30 minutes in a vacuum oven to yield 7.15 grams of benzeneselenol, sodium salt.

A large test tube was charged with all of the benzeneselenol, sodium salt, produced above and 7.20 grams of dimethyl carbonate. An immediate exotherm was noted. Gentle heating to a temperature in the range of from about 45° C. to about 50° C. was applied for about 2 minutes using a heat gun. The reaction mixture was allowed to settle; some white solid was visible. About 25 cubic centimeters of dry diethyl ether was added and the reaction mixture was filtered. Low boiling materials were removed at about 40° C. in a Büchi rotating evaporator under the vacuum provided by a water aspirator. The product remaining in the flask of the evaporator weighed 5.82 grams. Gas chromatographic analysis showed the product to contain 97.9 area percent methylselenobenzene.

Although the present invention has been described with reference to specific details of certain embodiments thereof, it is not intended that such details should be regarded as limitations upon the scope of the invention except insofar as they are included in the accompanying claims.

I claim:

1. A method comprising reacting organic selenol or salt thereof with organic carbonate represented by the formula

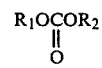

to produce organic selenoether, wherein $R_1$ and $R_2$ are each independently monovalent organic grups which may be the same or different, and wherein the alpha carbon of at least one $R_1$ and $R_2$ is substantially sterically unhindered.

2. The method of claim 1 wherein $R_1$ is alkyl, alpha,-beta-saturated alkenyl, aralkyl, (cycloalkyl)alkyl, cycloalkyl or lower aryl, and $R_2$ is alkyl, alpha,beta-saturated alkenyl, aralkyl or (cycloalkyl)alkyl.

3. The method of claim 1 wherein a. $R_1$ is alkyl having from 1 to about 20 carbon atoms, alpha,beta-saturated alkenyl having from 3 to about 10 carbon atoms, aralkyl wherein the aryl portion contains from 6 to about 10 carbon atoms and the alkyl portion contains from 1 to about 10 carbon atoms, (cycloalkyl)alkyl wherein the cycloalkyl portion contains from about 6 to about 8 carbon atoms and the alkyl portion contains from 1 to about 10 carbon atoms, cycloalkyl having from about 6 to about 8 carbon atoms, or lower aryl having from 6 to about 10 carbon atoms; and b. $R_2$ is alkyl having from 1 to about 20 carbon atoms, alpha,beta-saturated alkenyl having from 3 to about 10 carbon atoms, aralkyl wherein the aryl portion contains from 6 to about 10 carbon atoms and the alkyl portion contains from one to about 10 carbon atoms, or (cycloalkyl)alkyl wherein the cycloalkyl portion contains from about 6 to about 8 carbon atoms and the alkyl portion contains from 1 to about 10 carbon atoms.

4. The method of claim 1 wherein $R_1$ and $R_2$ are each independently alkyl having from 1 to about 10 carbon atoms.

5. The method of claim 1 wherein $R_2$ is methyl.

6. The method of claim 1 wherein $R_2$ is ethyl

7. The method of claim 1 wherein said organic carbonate is dimethyl carbonate.

8. The method of claim 1 wherein said organic carbonate is diethyl carbonate.

9. The method of claim 1 wherein said organic carbonate is diallyl carbonate.

10. The method of claim 1 wherein said reaction is conducted in the presence of catalyst.

11. The method of claim 10 wherein said catalyst is nitrogen-containing heterocyclic catalyst.

12. The method of claim 10 wherein said catalyst is 4-(dimethylamino)pyridine.

13. The method of claim 10 wherein said catalyst is pyridine.

14. The method of claim 10 wherein the equivalent ratio of said catalyst to said organic selenol or salt thereof initially present is in the range of from about 0.005:1 to about 0.5:1.

15. The method of claim 1 wherein said reaction is conducted at a temperature in the range of from about 0° C. to about 100° C.

16. The method of claim 1 wherein said reaction is conducted at a pressure in the range of from about zero to about 2500 kilopascals, gauge.

17. The method of claim 1 wherein said reaction is conducted in the presence of extrinsic solvent.

18. The method of claim 17 wherein the weight ratio of said extrinsic solvent to said organic selenol or salt thereof initially present is in the range of from about 0.01:1 to about 20:1.

19. The method of claim 1 wherein said reaction is neat.

* * * * *